(12) United States Patent
Vold et al.

(10) Patent No.: US 9,629,749 B2
(45) Date of Patent: Apr. 25, 2017

(54) ILLUMINATED TREATMENT PROBE FOR DELIVERING LASER ENERGY

(71) Applicant: IRIDEX Corporation, Mountain View, CA (US)

(72) Inventors: Steven D. Vold, Bentonville, AR (US); Kenneth A. Peartree, Danville, CA (US); David Buzawa, San Jose, CA (US)

(73) Assignee: IRIDEX Corporation, Mountain View, CA (US)

( * ) Notice: Subject to any disclaimer, the term of this patent is extended or adjusted under 35 U.S.C. 154(b) by 29 days.

(21) Appl. No.: 14/630,561

(22) Filed: Feb. 24, 2015

(65) Prior Publication Data

US 2015/0305938 A1 Oct. 29, 2015

Related U.S. Application Data

(60) Provisional application No. 61/945,385, filed on Feb. 27, 2014, provisional application No. 62/018,352, filed on Jun. 27, 2014.

(51) Int. Cl.
*A61F 9/008* (2006.01)

(52) U.S. Cl.
CPC ... *A61F 9/00821* (2013.01); *A61F 2009/00868* (2013.01); *A61F 2009/00891* (2013.01)

(58) Field of Classification Search
CPC ......... A61F 9/008; A61B 19/00; A61B 17/32; A61B 17/36
See application file for complete search history.

(56) References Cited

U.S. PATENT DOCUMENTS 5,121,740 A * 6/1992 Uram ............... A61B 1/00165
  600/108
5,372,595 A 12/1994 Gaasterland et al.
(Continued)

FOREIGN PATENT DOCUMENTS

WO  2015130821  9/2015

OTHER PUBLICATIONS

International Search Report and Written Opinion mailed Jan. 22, 2016 for corresponding PCT application, PCT/US2015/017573 filed Feb. 25, 2015, 10 pages.

*Primary Examiner* — William Thomson
*Assistant Examiner* — Victor Shapiro
(74) *Attorney, Agent, or Firm* — Kilpartick Townsend & Stockton LLP

(57) ABSTRACT

The present invention generally relates systems, methods, and devices for treating an eye of a patient. In some embodiments, a system may be provided that includes a console for generating a treatment laser and an illumination light. The system may further include a treatment probe for delivering the illumination light to an eye so as to illuminate the ciliary process of the eye. With the illuminated ciliary process, the treatment probe may be aligned to deliver the treatment laser from the console to the ciliary process of the eye for the purpose of treating a patient for glaucoma. In some embodiments, a treatment probe may be provided with an illumination fiber for delivering light to specific portions of the eye or at desired angles in order to illuminate the ciliary process. In some embodiments a treatment probe may be configured to cooperate with a removable light pen for eye illumination.

13 Claims, 13 Drawing Sheets

(56) References Cited

U.S. PATENT DOCUMENTS

| | | | | |
|---|---|---|---|---|
| 5,478,338 A | * | 12/1995 | Reynard | A61F 9/00745 606/15 |
| 5,514,125 A | * | 5/1996 | Lasser | A61F 9/00781 606/16 |
| 2008/0107384 A1 | | 5/2008 | Nadolski et al. | |
| 2010/0076419 A1 | | 3/2010 | Chew et al. | |

* cited by examiner

ILLUMINATED TREATMENT PROBE FOR DELIVERING LASER ENERGY

CROSS REFERENCE TO RELATED APPLICATION DATA

The present application claims the benefit under 35 USC §119(e) of U.S. Provisional Appln. Nos. 61/945,385 filed Feb. 27, 2014 and 62/018,352 filed Jun. 27, 2014; the full disclosures which are incorporated herein by reference in their entirety for all purposes.

BACKGROUND OF THE INVENTION

Field of the Invention

The present invention is directed generally to medical devices, systems, and methods, particularly for treatment of an eye. In particular, embodiments of the present invention are directed toward contact probes for the delivery of laser energy, and more particularly to contact probes that are used for lowering the intraocular pressure (IOP) in human eyes afflicted with glaucoma.

Glaucoma is a leading cause of blindness. Glaucoma involves the loss of retinal ganglion cells in a characteristic pattern of optic neuropathy. Untreated glaucoma can lead to permanent damage of the optic nerve and resultant visual field loss, which can progress to blindness. The loss of visual field due to glaucoma often occurs gradually over a long time and may only be recognized when the loss is already quite advanced. Once lost, this damaged visual field can never be recovered.

Raised intraocular pressure (IOP) is a significant risk factor for developing glaucoma. IOP is a function of production of aqueous humor by the ciliary body of the eye and its drainage through the trabecular meshwork and all other outflow pathways including the uveoscleral pathway. Aqueous humor is a complex mixture of electrolytes, organics solutes, and other proteins that supply nutrients to the non-vascularized tissues of the anterior chamber of the eye. It flows from the ciliary bodies into the posterior chamber, bounded posteriorly by the lens and the ciliary zonule and bounded anteriorly by the iris. Aqueous humor then flows through the pupil of the iris into the anterior chamber, bounded posteriorly by the iris and anteriorly by the cornea. In the conventional aqueous humor outflow path, the trabecular meshwork drains aqueous humor from the anterior chamber via Schlemm's canal into scleral plexuses and the general blood circulation. In open angle glaucoma there is reduced flow through the trabecular meshwork. In angle closure glaucoma, the iris is pushed forward against the trabecular meshwork, blocking fluid from escaping.

Uveoscleral outflow is a non-conventional pathway that is assuming a growing importance in the management of glaucoma. In uveoscleral outflow, aqueous humor enters the ciliary muscles from the anterior chamber and exits through the supraciliary space and across the anterior or posterior sclera. Uveoscleral outflow may contribute significantly to total aqueous humor outflow.

Currently, glaucoma therapies aim to reduce IOP by either limiting the production of aqueous humor or by increasing the outflow of aqueous humor. Medications such as beta-blockers, carbonic anhydrase inhibitors, etc., are used as the primary treatment to reduce the production of aqueous humor. Medications may also be used as the primary therapy to increase the outflow of the aqueous humor. Miotic and cholinergic drugs increase the trabecular outflow, while prostaglandin drugs, for example, Latanoprost and Bimatoprost, increase the uveoscleral outflow. These drugs, however, are expensive and have undesirable side effects, which can cause compliance-dependent problems over time.

Surgery may also be used to increase the outflow or to lower the production of aqueous humor. Laser trabeculoplasty is the application of a laser beam over areas of the trabecular meshwork to increase the outflow. Cyclocryotherapy and laser cyclophotocoagulation are surgical interventions over the ciliary processes to lower the production of aqueous humor. Although they may be effective, these destructive surgical interventions are normally used as a last resource in the management of glaucoma due to the risk of the severe complication of phthisis bulbi. Other adverse side effects of cyclodestructive surgical procedures may include ocular hypotony and inflammation of the anterior eye segment, which may be associated with an increased incidence of macula complications. Still other adverse side effects include transient hyphaema and exudates in the anterior chamber, uveitis, visual loss, and necrotizing scleritis.

In laser transscleral cyclophotocoagulation, a continuous wave (CW) of high intensity infrared laser energy is directed toward selected portions of the pars plicata region of the ciliary body, structures under the scleral layers and the overlying conjunctiva. Selected portions of the ciliary body and related processes are permanently destroyed, thereby decreasing the overall production of aqueous humor. Laser energy may be directed through air to a patient seated at a special slit lamp. Alternatively, laser energy may be delivered through the use of fiber optic handpieces placed in contact with the patient's eyeball. In both laser energy delivery methods, however, accurately and repeatedly directing a laser beam a subsurface non-visible target such as the ciliary body can be challenging for a surgeon. Thus, contact handpiece probes (for example, the G-Probe available through IRIDEX Corporation of Mountain View, Calif. and described in U.S. Pat. No. 5,372,595, the full disclosure of which is incorporated herein by reference in its entirety) have been designed to facilitate the aiming of a laser toward the pars plicata region of the ciliary body. The G-Probe, for example, has special contours that facilitate consistent placement and aiming of the probe relative to external landmark structures of the eye, thereby guiding a treatment and decreasing the likelihood of incidental laser exposure to unintended structures.

While the prior systems, methods, and devices have provided advancements in the art, further improvements are desired.

SUMMARY OF THE INVENTION

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings and each claim.

In some embodiments, a method for treating an eye of a patient is provided—the eye having a cornea, a pupil, a visual axis, and a ciliary process, and being afflicted with glaucoma. The method may include providing a treatment probe for treating the eye of the patient. The treatment probe may include a treatment fiber for delivering a treatment laser energy to the eye from a distal end of the treatment fiber. The treatment probe may further include an illumination light conduit for delivering illuminating light to the eye from a distal end of the illumination light conduit. The treatment probe may further include a contact surface for coupling with a surface of the eye. The method may further include placing the contact surface of the treatment probe on the surface of the eye of the patient. An edge of the ciliary process of the eye may be illuminated by directing illuminating light from the distal end of the illumination light conduit of the treatment probe to the eye. The distal end of the treatment fiber of the treatment probe may be positioned per the illuminated edge of the ciliary process. The method may further include delivering the treatment laser energy to the eye from the distal end of the treatment fiber while the treatment probe is positioned per the illuminated edge of the ciliary process.

In some embodiments, the edge of the ciliary process of the eye may be illuminated by delivering illumination light at an angle ranging from 30-60° from the visual axis of the eye. In some embodiments, the edge of the ciliary process of the eye may be illuminated by delivering illumination light through the cornea and parallel to the visual axis of the eye of the patient. Optionally, the illumination light may be delivered through the pupil of the eye of the patient. In some embodiments, the edge of the ciliary process of the eye may be illuminated by delivering illumination light through the cornea directly at the angle of the anterior chamber.

In some embodiments, the distal end of the illumination light conduit may be manually adjustable such that the illumination light conduit is reconfigurable to deliver light at different angles relative to the eye and/or to different regions of the eye. Thus, in some embodiments, the method includes adjusting the distal end of the illumination light conduit such that illumination light is delivered through the cornea and parallel to the visual axis of the eye while the contact surface of the probe is placed on the surface of the eye. Optionally, the distal end of the illumination light conduit may be adjusted such that illumination light is delivered through the pupil of the eye. In some embodiments, the distal end of the illumination light conduit may be adjusted such that illumination light is delivered at an angle ranging from 30-60° from the visual axis of the eye while the contact surface of the probe is placed on the surface of the eye. In some embodiments, the distal end of the illumination light conduit may be adjusted such that illumination light is delivered directly at the angle of the anterior chamber while the contact surface of the probe is placed on the surface of the eye.

In some embodiments, a treatment probe for treating an eye of a patient for glaucoma is provided. The treatment probe may include an elongate body defining a handle having a proximal end and a distal end. A treatment fiber may be housed in the elongate body and configured for delivering a treatment laser to energy the eye from a distal end of the treatment fiber. An illumination light conduit may be housed in the elongate body and configured for delivering illuminating light to the eye from a distal end of the illumination light conduit. The treatment probe may further include a contact surface for coupling with a surface of the eye. The distal end of the illumination light conduit may be configured to deliver illumination light at an angle ranging from 30-60° from the visual axis of the eye when the contact surface of the treatment probe couples with the surface of the eye. Optionally, the distal end of the illumination light conduit may be configured to deliver illumination light through the cornea and parallel to the visual axis of the eye of the patient when the contact surface of the treatment probe couples with the surface of the eye. In some embodiments, the distal end of the illumination light conduit may be configured to deliver illumination light through the pupil of the eye when the contact surface of the treatment probe couples with the surface of the eye. In some embodiments, the distal end of the illumination light conduit may be configured to deliver illumination light through the cornea directly at the angle of the anterior chamber when the contact surface of the treatment probe couples with the surface of the eye.

In some embodiments, the distal end of the illumination light conduit may be manually adjustable such that the illumination light conduit is reconfigurable to deliver light at different angles relative to the eye and/or to different regions of the eye. Optionally, the illumination light conduit may branch off such that the illumination light conduit comprises a plurality of distal ends for delivering illumination light from a plurality of points.

In some embodiments, the distal end of the illumination light conduit may terminate at the contact surface of the treatment probe. In some the illumination the light conduit may branch out such that the illumination light conduit comprises a first distal end and a second distal end for delivering illumination light from a plurality of points. The first distal end and the second distal end of the illumination light conduit may terminate on both sides of the distal end of the treatment fiber such that illumination light is directed in the same plane as the treatment laser.

In some embodiments, a system for treating an eye of a patient for glaucoma is provided. The system may include a console for generating a treatment laser for treating the eye and for generating an illumination light for illuminating the ciliary body of the eye. The system may further include a treatment probe configured to operatively couple with the console to deliver the treatment laser energy and the illumination light from the console toward the eye of the patient. The treatment probe may include an elongate body defining a handle having a proximal end and a distal end. A treatment fiber may be housed in the elongate body and configured for delivering a treatment laser energy to the eye from a distal end of the treatment fiber. An illumination light conduit may be housed in the elongate body and configured for delivering illuminating light to the eye from a distal end of the illumination light conduit. The treatment probe may further include a contact surface for coupling with a surface of the eye.

In yet another embodiment, a treatment probe for treating an eye of a patient for glaucoma may be provided. The treatment probe may comprise an elongate body defining a handle having a proximal end and a distal end. A light source may be housed in the elongate body and have a light transmitting surface oriented for delivering a treatment beam to the eye from the distal end of the elongate body. The treatment probe may also include an illumination light source housed in the elongate body and configured for delivering illuminating light to the eye from a distal end of the body. For example, a treatment probe may house one or more laser diodes, one or more light emitting diodes, or combinations thereof for providing illumination light and treatment light to an eye.

In some embodiments, a contact surface may have a convex configuration for coupling with a surface of the eye. The convex contact surface may be aligned with the target region by illuminating the target region with illumination light and aligning the convex contact surface per the illuminated target region. The convex configuration may not conform to the surface of the eye and may facilitate sweeping or sliding of the treatment probe along the surface of the eye. Optionally, the treatment laser energy may be delivered while sliding the convex contact surface of the probe across the surface of the eye. In some embodiments, the convex contact surface may be slid by sliding the convex contact surface along an arc while maintaining the alignment of the treatment probe with the treatment region of the eye.

In some embodiments, the convex contact surface may be slid along an arc of less than 180° on a first region of the eye. Optionally, sliding the convex contact surface may comprise sliding along an arc of 140-160°. In some embodiments, the convex contact surface may be slid by sliding between 2-10 traverses along an arc in less than 60 seconds. Optionally, the convex contact surface may be slid by sliding between 5-10 traverses along the arc in 45-55 seconds. In some embodiments, the convex surface may be slid by sliding the convex contact surface along an arc of less than 180° on a second region of the eye—the second region of the eye being opposed from, and/or opposite from, the first region. In some embodiments, the treatment laser may comprise pulsed laser energy (e.g., pulsed infrared laser energy) as the convex contact surface is slid across the treatment region of the eye. The pulsed laser energy may preferably have a duty cycle of greater than 25% (or even 28%), often being between 25%-45% when delivering the laser treatment and moving the probe in a sliding manner. Preferably, the duty cycle may be between 28-32% when delivering the laser treatment. These ranges may be advantageous for transscleral treatment delivery.

In many embodiments, the convex contact surface does not conform to the sclera of the eye. Optionally, the distal end of the treatment fiber may protrude from the convex contact surface by more than 0.15 mm, often by no more than 0.4 mm from the convex contact surface. The protrusion, while somewhat contrary to the intended sliding use of the device, may significantly enhance optical coupling efficiency between the probe and the target tissue, while a rounded fiber end limited protrusion distance (combined with the adjacent convex contact surface) may facilitate smooth sliding of the convex contact surface along the surface of the eye despite the protrusion. In some embodiments, the treatment laser energy may be delivered by delivering a train of laser beam pulses so as to induce a therapeutic response without coagulation—the beneficial response mitigating of pressure within the eye.

In some embodiments, the convex contact surface has a circular cross-section with a radius of less than 12 mm. Optionally the cross-sectional radius may be between 2-10 mm. In some embodiments, the convex contact surface of the contact member may have a 5-50 mm radius of curvature, or may be planar. An edge between the contact surface and the distal end of the treatment probe may be rounded to further facilitate sweeping/sliding of the treatment probe along the surface of an eye.

The invention will be better understood on reading the following description and examining the figures that accompany it. These figures are provided by way of illustration only and are in no way limiting on the invention.

DETAILED DESCRIPTION

The subject matter of embodiments of the present invention is described here with specificity, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described.

Figure 1:
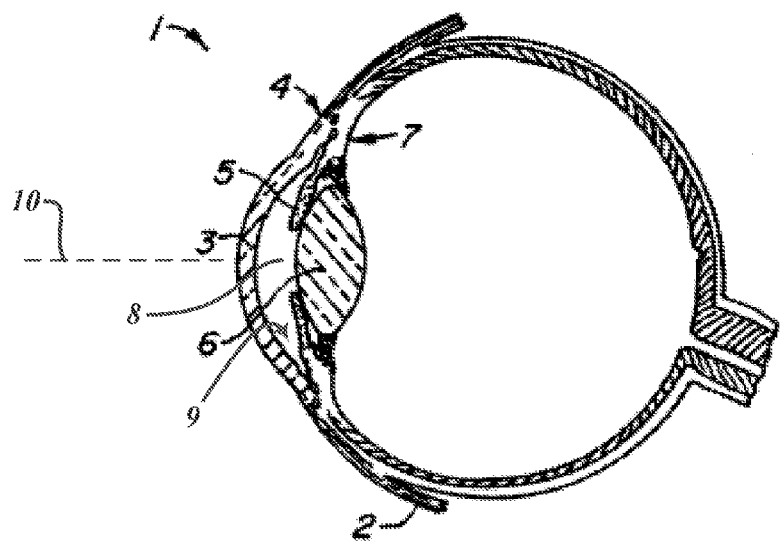
FIG. 1 shows general anatomy of an eye of a patient.

FIG. 1 shows the anatomy of an eye 1 with relevant parts labeled to provide anatomical references. The sclera 2 is a tough sheath around the eye which meets the cornea 3 at a circular junction called the limbus 4. Behind the cornea 3 lies the iris 5, the lens 6 and the ciliary body and related processes 7. The anterior chamber is the fluid-filled compartment within the eye 1 just in front of the pupil 8. Viewed in profile, the anterior chamber is bounded by the domed cornea 3 in front and by the colored iris 5 behind. Where the cornea 3 and the iris 5 converge they form an angle 9 referred to herein as the angle of the anterior chamber. Further eye 1 may have a visual/optical axis 10.

Embodiments described herein provide systems, methods, and devices for achieving trans-illumination of the edge of the ciliary process 7 during the application of treatment lasers energy (e.g., infrared laser power) to the ciliary process 7. While prior treatment methods and devices were able to generally estimate the location of the ciliary process 7 based solely on an offset distance from a patient's limbus 4, it has been found that the distance from the limbus 4 to the ciliary process 7 can vary significantly from patient to patient. Thus, illumination of the ciliary process 7 during the application of a treatment laser energy may provide a visual indication to an operator as to the exact location of the ciliary process 7. Thus operators may account for the anatomical variations between patients and facilitate more accurate treatments of the ciliary process 7.

Figure 2:
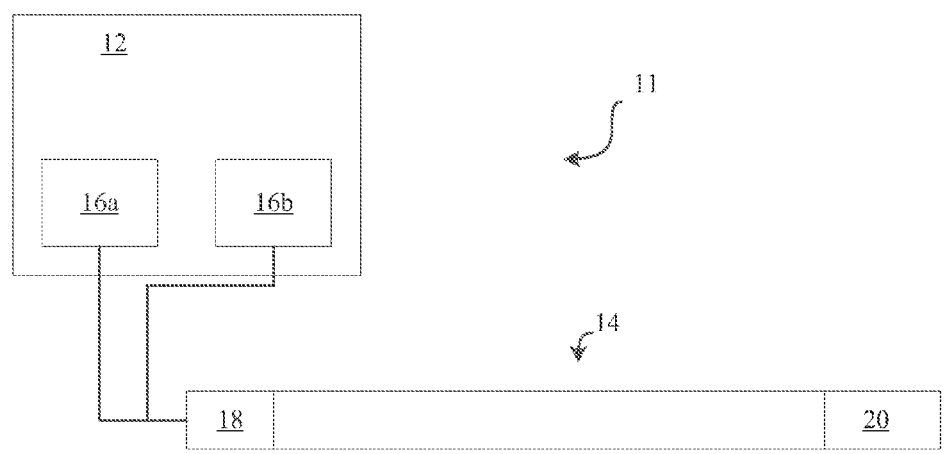
FIG. 2 shows a simplified schematic diagram of a laser treatment system according to some embodiments.

FIG. 2 shows a simplified schematic diagram of an exemplary system 11 for treating an eye of a patient for glaucoma according to some embodiments of the invention. Exemplary system 11 may comprise a console 12 coupled with a treatment probe 14. Console 12 may be configured to generate a treatment laser energy for treating the eye 1. The console 12 may, for example, generate a 810 nm infrared treatment laser energy. Additionally, in some embodiments, console 12 may be configured to generate illumination light (e.g., white light) for illuminating various parts of the eye 1. In some embodiments, console 12 includes one or more outlets 16a, 16b for outputting the treatment laser and/or illumination light generated by console 12 to a coupled treatment probe 14. The one or more outlets 16a, 16b may be configured to couple with the treatment probe 14 by receiving a proximal connection end 18 of the treatment probe 14. For example, in some embodiments, outlet 16a may output a treatment laser energy to a coupled treatment probe 14 for delivery to an eye 1 and outlet 16b may output the illumination light to a coupled treatment probe 14 for illumination of the ciliary process of the eye 1. Thus, a system user may selectively disconnect the treatment probe 14 from one or more of the outlets 16a, 16b. For example, when procedure does not require illumination light, the system user may easily deactivate such a feature by disconnecting the treatment probe 14 from outlet 16b. Additionally, or alternatively, the console 12 may be configured to allow a user to selectively control a brightness of the illumination light. Once coupled to the console 12, treatment probe 14 may deliver the treatment laser and/or illumination light from the console 12 to a distal treatment end 20 of the treatment probe 14 via optical waveguides, fiber optics, light conduits, light guides, light tubes, or the like.

Figure 3A:
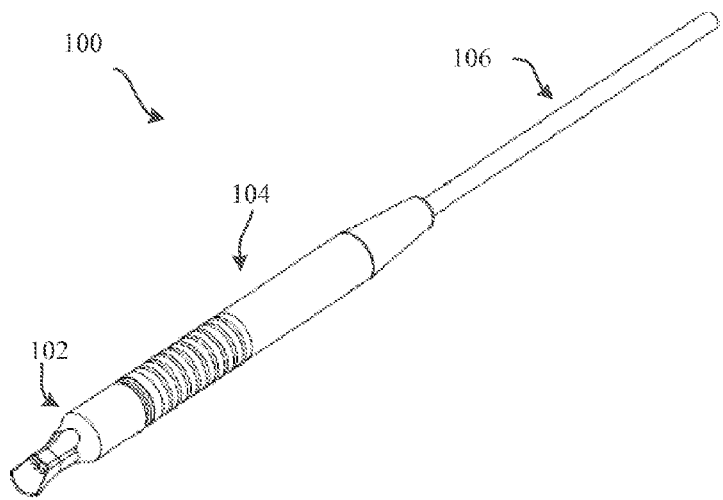
FIGS. 3A-3D show an exemplary treatment probe according to some embodiments of the invention.
Figure 3B:
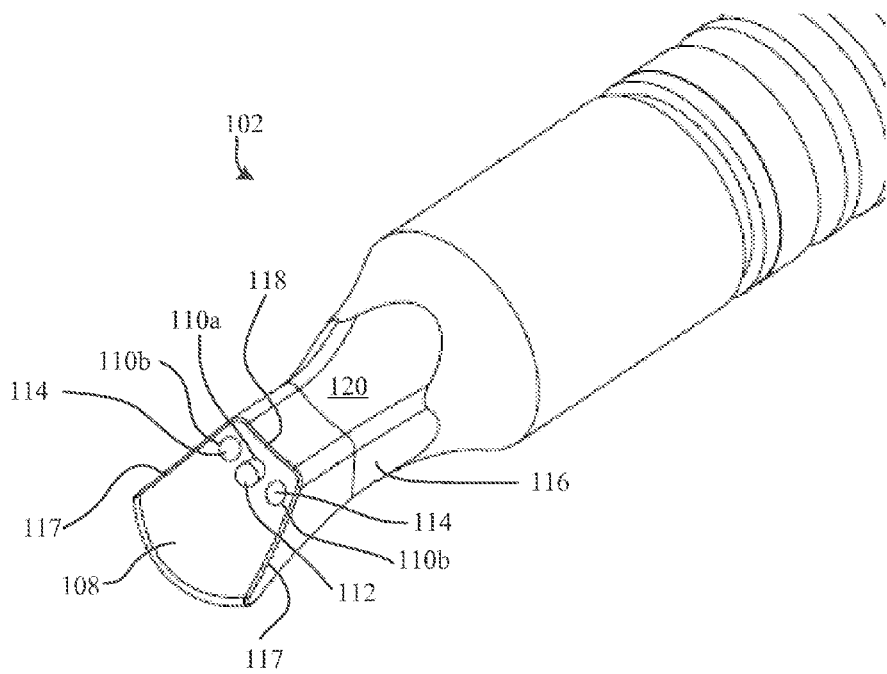

FIGS. 3A-3D show an exemplary treatment probe 100 according to some embodiments of the invention. FIG. 3A shows a distal portion of the exemplary treatment probe 100. As illustrated, exemplary treatment probe 100 includes an output tip 102 coupled with a distal end of a handle 104 and a cord 106 configured to couple the handle 104 to a console (e.g., console 12 of FIG. 2). Handle 104 may be configured for manipulation by an operator and may include one or more buttons (not shown) for controlling the delivery of the treatment laser and/or illumination light from a console 12 to an eye 1 of a patient. FIG. 3B shows a close up view of the exemplary output tip 102. The output tip 102 of the treatment probe 100 has a contact surface 108 for coupling with a surface of the eye 1. In some embodiments, a portion of the contact surface 108 may be constructed out of a transparent material so as to allow a user to visually observe the underlying eye tissues coupled with the contact surface 108. The contact surface 108 may contain an opening 110a for a distal end of a fiber optic 112 and openings 110b for distal ends of light pipe(s) 114. In the illustrated embodiment, opening 110a may be equidistant from either side 117 of the contact surface 108. Further, openings 110b may be equally and laterally spaced on each side of opening 110a.

Accordingly, in some embodiments, the fiber optic 112 may terminate at the contact surface 108 and may be configured to deliver a treatment laser energy directly to eye tissues coupled therewith. While illustrated as including a single fiber optic 112, it should be understood that other embodiments may have a plurality of fiber optics 112 for delivering treatment laser energy to a plurality of locations.

Also as illustrated in FIG. 3B, light pipes 114 may also terminate at the contact surface 108 and may thus apply illumination directly to the treatment site in order to illuminate the edge of the ciliary process 7 below the sclera 2 so as to facilitate the alignment of the distal end of the treatment fiber 112. The illumination fibers may be adhered to the output tip 102 using biocompatible adhesives for example. In some embodiments, the distal ends of the light pipe(s) 114 may be polished flush with contact surface 108.

In the exemplary embodiment 100, two openings 110b are provided for a two distal ends of one or more light pipes 114. Some embodiments may comprise a plurality of light pipes 114 that each have distal ends that terminate at a contact surface 108. Alternatively, in some embodiments, a single light pipe 114 may branch off toward the distal portion of the treatment probe 100 to a plurality of distal ends. While illustrated as including two openings 110b for light pipe 114, it should be understood that other embodiments may include a single opening 110b for a light pipe 114, or more than two openings 110b (e.g., three, four, five, or more openings) for several distal ends of light pipe(s) 114.

Figure 3C:
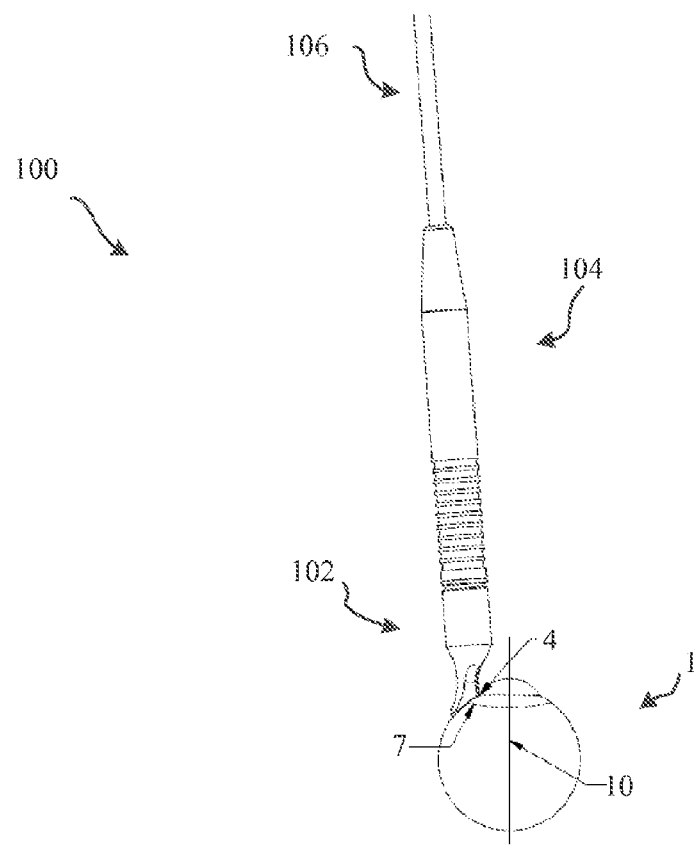

As discussed above, contact surface 108 may couple with a surface of the eye 1. In some embodiments, the contact surface 108 may be contoured to register against the eye 1 at the limbus 4. For example, in some embodiments, the contact surface 108 may be contoured to generally conform to the shape of the eye 1 at the limbus 4 when the axis of the treatment probe 100 is parallel to the visual/optic axis 10 of the eye 1. This may be closely approximated as a concave spherical segment of radius 12.5 mm to 12.7 mm, the spherical center being located about 6.7 mm to 6.9 mm below the opening for the fiber optic 112. A contact surface 108 with such a configuration may facilitate the alignment of the exemplary treatment probe 100 with the eye 1 as shown in FIG. 3C. FIG. 3C shows the exemplary treatment probe 100 positioned against an eye 1. When the contoured contact surface 108 is registered against the eye 1 at the limbus 4, the treatment probe 100 may be aligned so as to direct treatment laser energy substantially parallel to the eye's visual axis 10.

Contact surface 108 may further include side edges 117 that are aligned as ray segments from the optic axis 10 of the eye 1. Such a configuration may be used to define treatment spacing edges and/or aid in the visual alignment of the treatment probe 100 around the eye 1. As shown and described above, the opening 110a and the distal end of the fiber optic 112 may be equidistant from either side 117 of the contact surface 108. In some embodiments, this half width may be chosen to be roughly equal to a desired treatment side spacing. After a first site is treated, each successive site may be selected by aligning a side edge 117 of the probe contact surface 108 with the lesion created at the previous site. In its simplest form, one lateral edge 117 may be a treatment spacing edge; used in the above described manner, the distance between treatment sites may be equal to the distance between the treatment spacing edge and the distal end of the fiber optic 112. A side relief 116 may extend back from the treatment spacing edge so that the edge may be visible during use.

In some embodiments, contact surface 108 may include a placement edge 118 with a placement contour 120 extending away from the placement edge 118 to the body of the handle 104. The placement edge 118 may be shaped to conform to the limbus 4, circularly concave with a radius of about 5.5-6.0 mm and about 1.2 mm from opening 110a. Knowing the distance between placement edge 118 and opening 110a may facilitate a desired alignment of the distal end of the fiber optic 112 with the eye's ciliary body 7. In some embodiments, a visual indicator (e.g., a line or groove) may be provided along the placement contour 120 that may provide a visual indication to an operator of the lateral position of the opening 110a. As mentioned above, some embodiments may have an output tip 102 and/or a contact surface 108 constructed partially or entirely out of a transparent material such that a user can visualize an alignment between opening 110a/fiber 112 and the eye tissues.

Figure 3D:
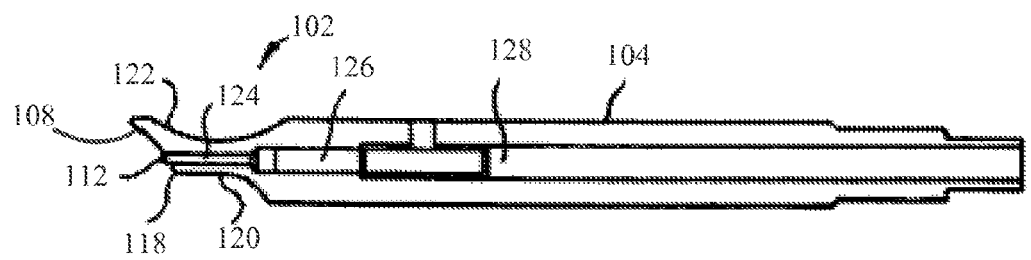

FIG. 3D shows an cross-sectional view of exemplary treatment probe 100. In some embodiments, an eyelid lifting contour 122 may be provided. The eyelid lifting contour 122 may comprise a circular concavity in an upper surface of output tip 102. The circular concavity may have a radius about 25 mm and a center of curvature located about 31 mm above the axis of the treatment probe 100. The eyelid lifting contour 122 may be any generally concave or scoop shaped relief of roughly the same size. Placement contour 120 may extend axially from placement edge 118. Fiber optic 112 is shown within a bore 124 and may extend slightly out from the contact surface 108. The output tip of fiber optic 112 may be polished flat. When contact surface 108 is registered against the eye 1, the protruding distal end of fiber optic 112 may indent the surface of the eye 1 and may squeeze out extracellular water, thus improving the transmission efficiency of the laser beam. The protrusion of the distal end of the fiber optic 112 may be anywhere from about 0.5 mm to about 1.0 mm, e.g., 0.75 mm. Also shown in FIG. 3D is a sheathed fiber optic portion 126 within a wider bore 128.

Figure 4A:
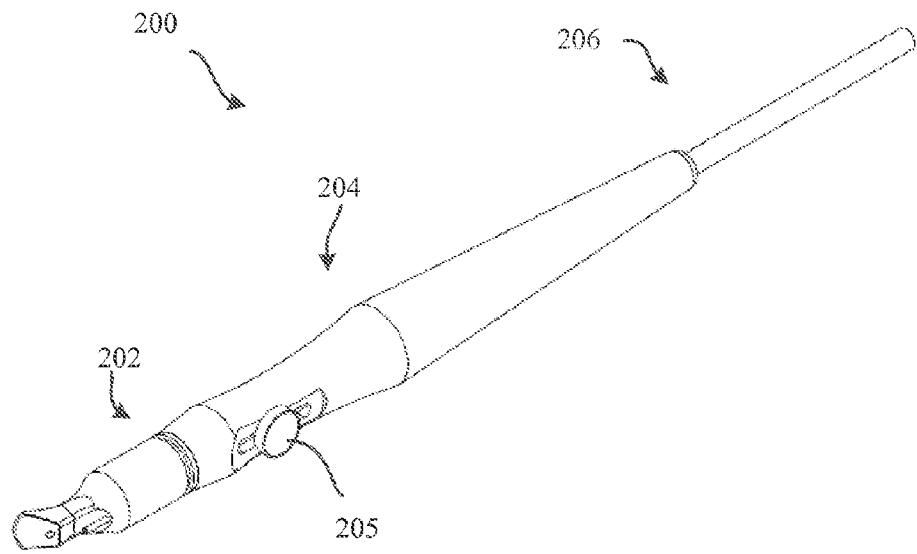
FIGS. 4A-4C show yet another exemplary treatment probe according to some embodiments of the invention.
Figure 4B:
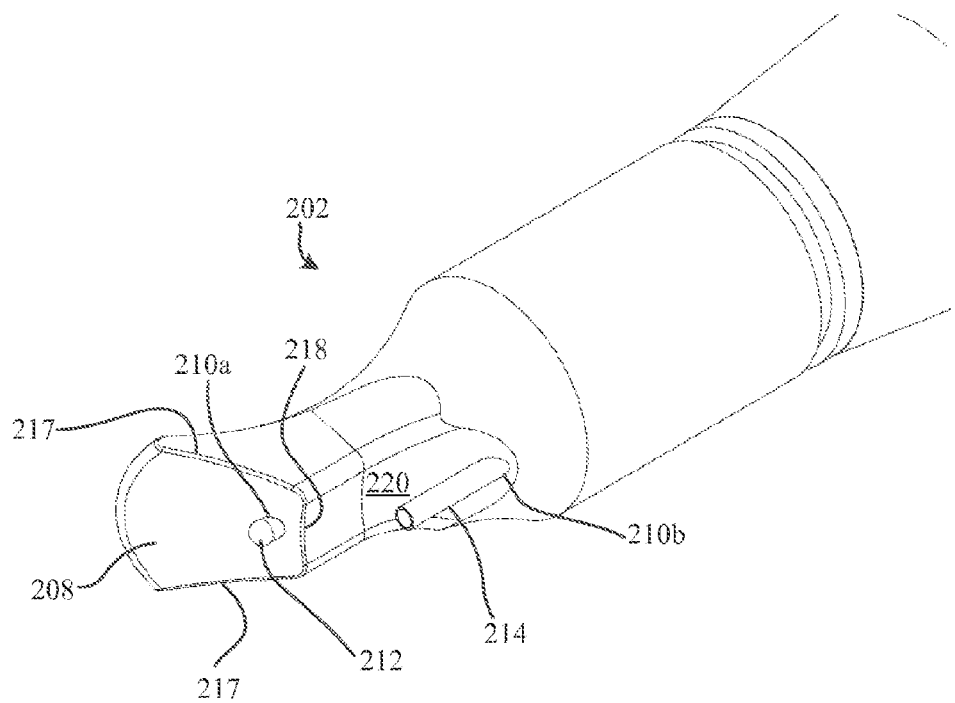
Figure 4C:
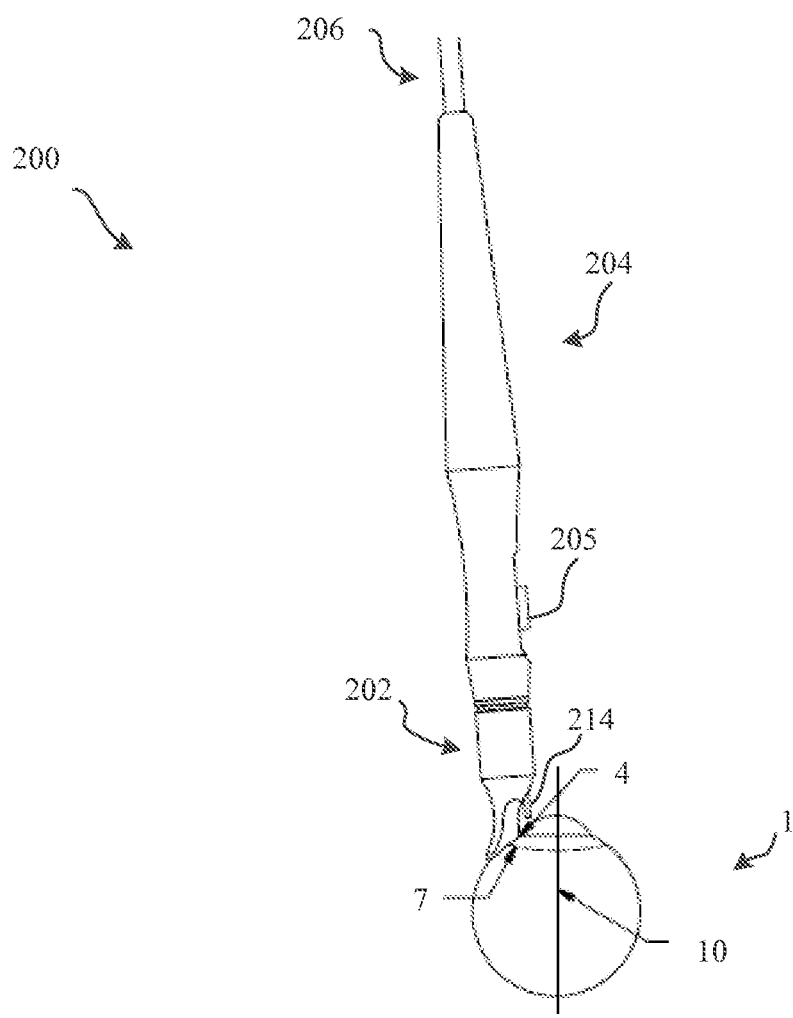

FIGS. 4A-4C illustrate yet another exemplary treatment probe 200. FIG. 4A shows a distal portion of treatment probe 200. FIG. 4B shows a close up view of an output tip 202 of treatment probe 200. FIG. 4C shows an exemplary placement of treatment probe 200 against a surface (e.g., sclera 2) of the eye 1. Treatment probe 200 may include an output tip 202 coupled with a distal end of a handle 204, and a cord 206 configured to couple handle 204 with a console (e.g., console 12 of FIG. 2). Treatment probe 200 may further include an output tip 202 with a contact surface 208 geometry (e.g., side edges 217, placement edge 218, placement contour 220, etc.) similar to output tip 102 that allows output tip 202 to rest against the sclera 2 and contour to the limbus 4 of the eye 1, as described above. Treatment probe 200 may further include a treatment fiber 212 and opening 210a similar to treatment probe 100. Treatment probe 200 may include a clearance hole 210b bored through the output tip approximately 0.1 inch closer to the visual axis 10 from an axis defined by the treatment fiber 212, so that a light pipe 214 may pass there through. In some embodiments, the illumination fiber may be adhered to the interior of the light pipe 214 and may pass through the fiber jacket. Treatment probe 200 may further include a button 205 on handle 204. Button 205 may be configured to provide user control of the application of illumination light and/or treatment laser energy to the eye 1. As can be seen in FIG. 4C, light pipe 214 may deliver illumination light in a direction parallel to and offset from the optical axis 10 of the eye 1 to illuminate the edge of the ciliary process 7. The illumination light from light pipe 214 may apply illumination through the cornea 3 to the angle of anterior chamber 9 of the eye 1. Optionally, in some embodiments, light pipe 214 may be manually adjustable to allow the probe 200 to be reconfigured for varying eye geometry, and/or for varying illumination. In some embodiments, probe 200 may be configured to deliver illumination light parallel to and along the visual axis 10 of the eye 1 so as to illuminate the ciliary body 7.

Figure 5A:
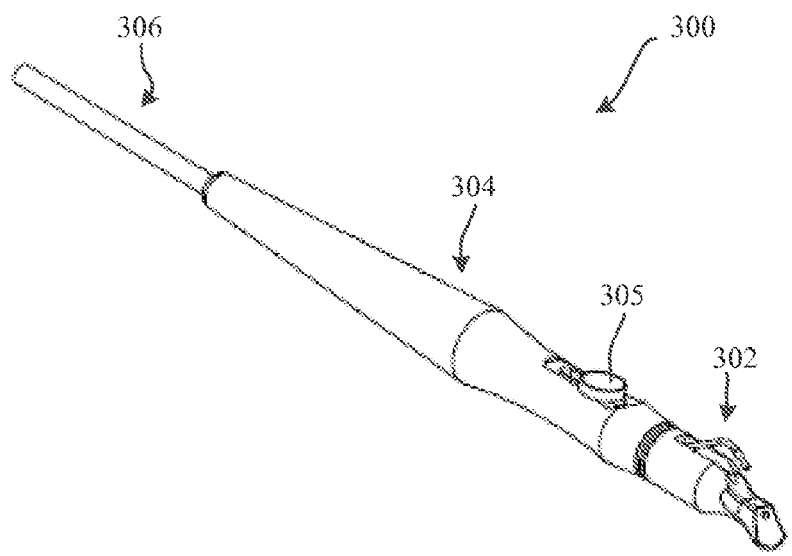
FIGS. 5A-5C show yet another exemplary treatment probe according to some embodiments of the invention.
Figure 5B:
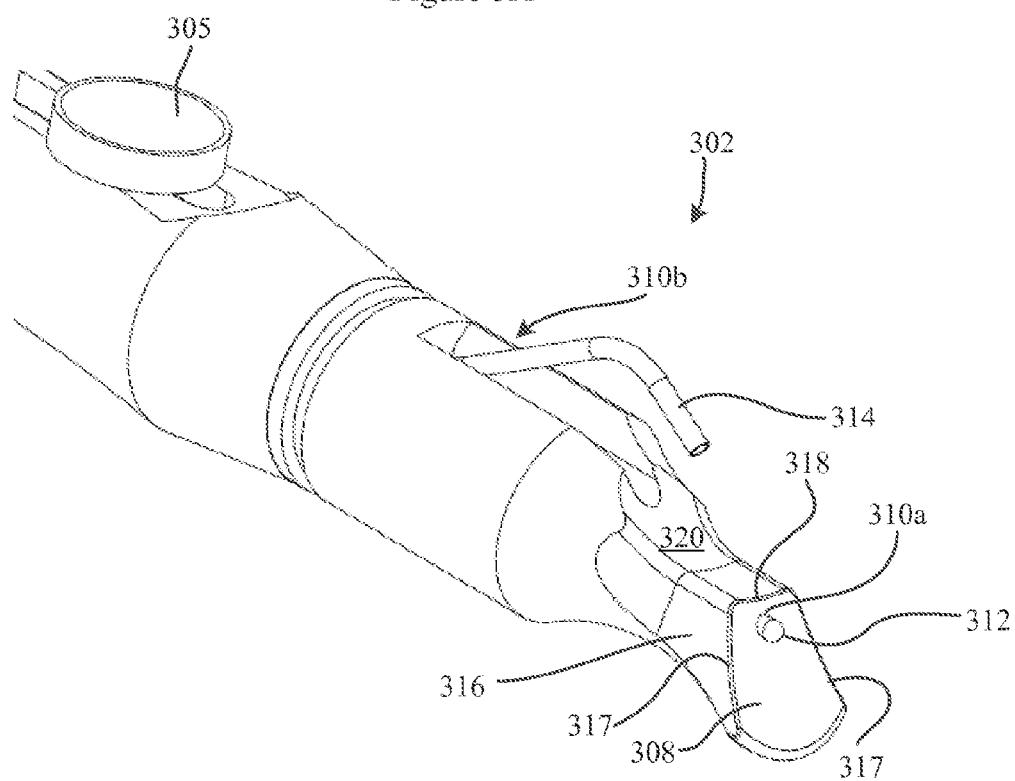
Figure 5C:
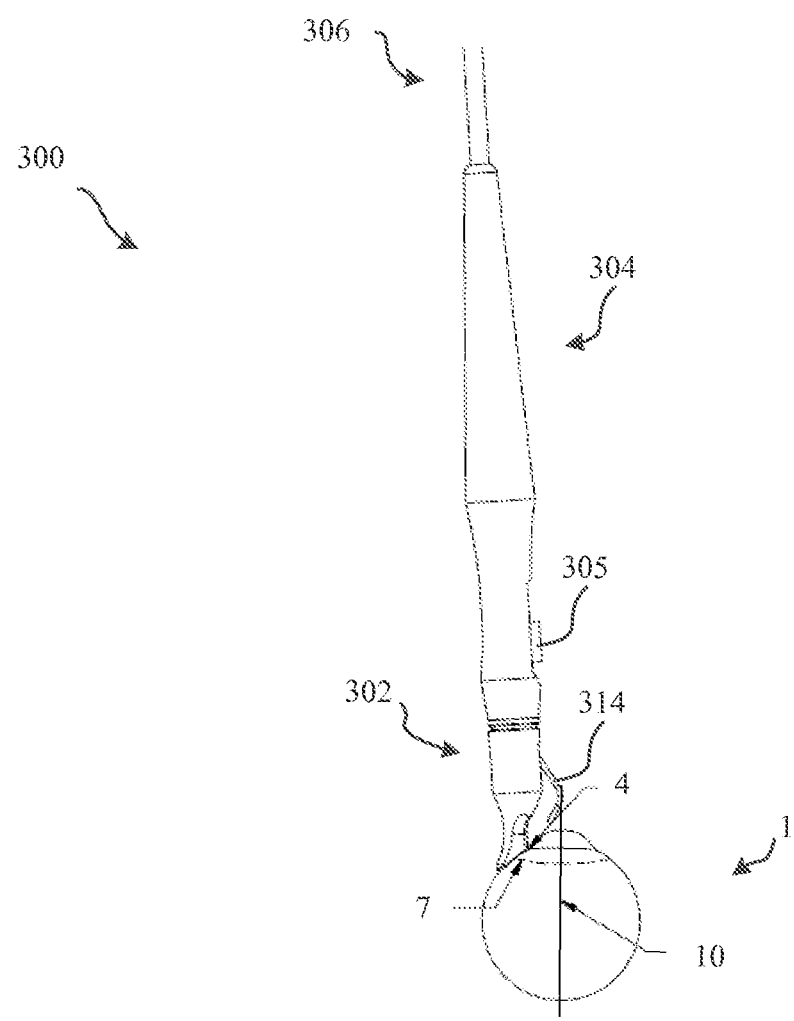

FIG. 5A-5C illustrate yet another exemplary treatment probe 300. FIG. 5A shows a distal portion of treatment probe 300. FIG. 5B shows a close up view of an output tip 302 of treatment probe 300. FIG. 5C shows an exemplary placement of treatment probe 300 against a surface of the eye 1. Treatment probe 300 may include an output tip 302 coupled with a distal end of a handle 304, and a cord 306 configured to couple handle 304 with a console (e.g., console 12 of FIG. 2). Treatment probe 300 may further include an output tip 302 with a contact surface 308 geometry (e.g., side relief 316, side edges 317, placement edge 318, placement contour 320, etc.) similar to output tip 102 that allows output tip 302 to rest against the sclera 2 and contour to the limbus 4 of the eye 1, as described above. Treatment probe 300 may further include a treatment fiber 312 and opening 310a similar to treatment probe 100. The treatment probe 300 may include a light pipe 314 similar to treatment probe 200, however, a clearance hole 310b may comprise an axially elongate slot along output tip 302 that exposes a length of light pipe 314. The length of light pipe 314 exposed may range between 1-5 cm. The distal end of the illumination light pipe 314 may be manually adjustable such that the illumination light pipe is reconfigurable to deliver light at different angles relative to the eye and/or to different regions of the eye. Further, a reconfigurable distal end of an illumination light pipe 314 may be advantageously accommodate for anatomical variation between patients and allow the light pipe 314 to be kept away from contact the cornea. In some embodiments, the light pipe 314 may have a semi-rigid portion to allow it to flex if contact is made with the cornea. The semi-rigid portion may mitigate risk of inadvertent damage to the cornea due to accidental contact. An axially elongated clearance hole 310b may expose a length of light pipe 314 that may be retracted without contacting output tip 302. The distal end of the light pipe 314 may be configured with a compound bend so that the light pipe 314 projects light at 30-60° angle from the visual axis 10 of the eye 1. A treatment probe 300 that projects light at such an angle may provide for better illumination of the angle of anterior chamber 9 and thus better illumination of the edge of the ciliary process 7. An angle between 30-60° may direct light through the cornea 3 and directly at the angle of anterior chamber 9. Treatment probe 300 may also include one or more buttons 305 for providing user control of the application of illumination light and/or treatment laser energy to the tissues of the eye 1.

Figure 6A:
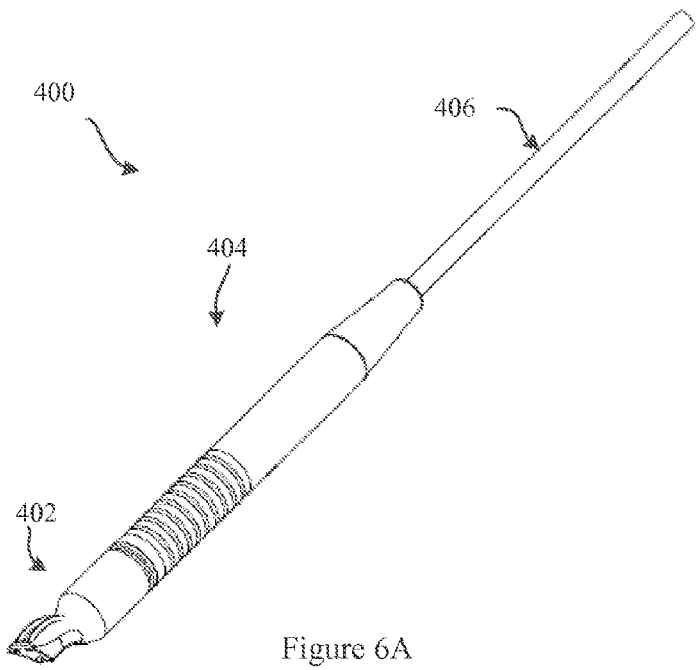
FIGS. 6A-6C show yet another exemplary treatment probe according to some embodiments of the invention.
Figure 6B:
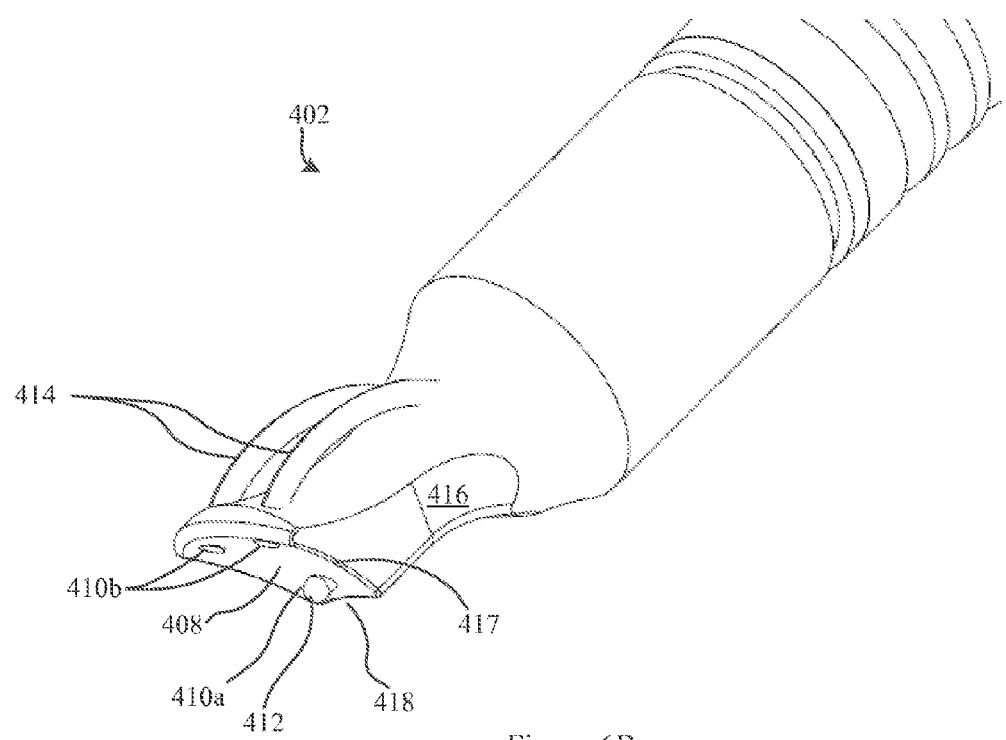
Figure 6C:
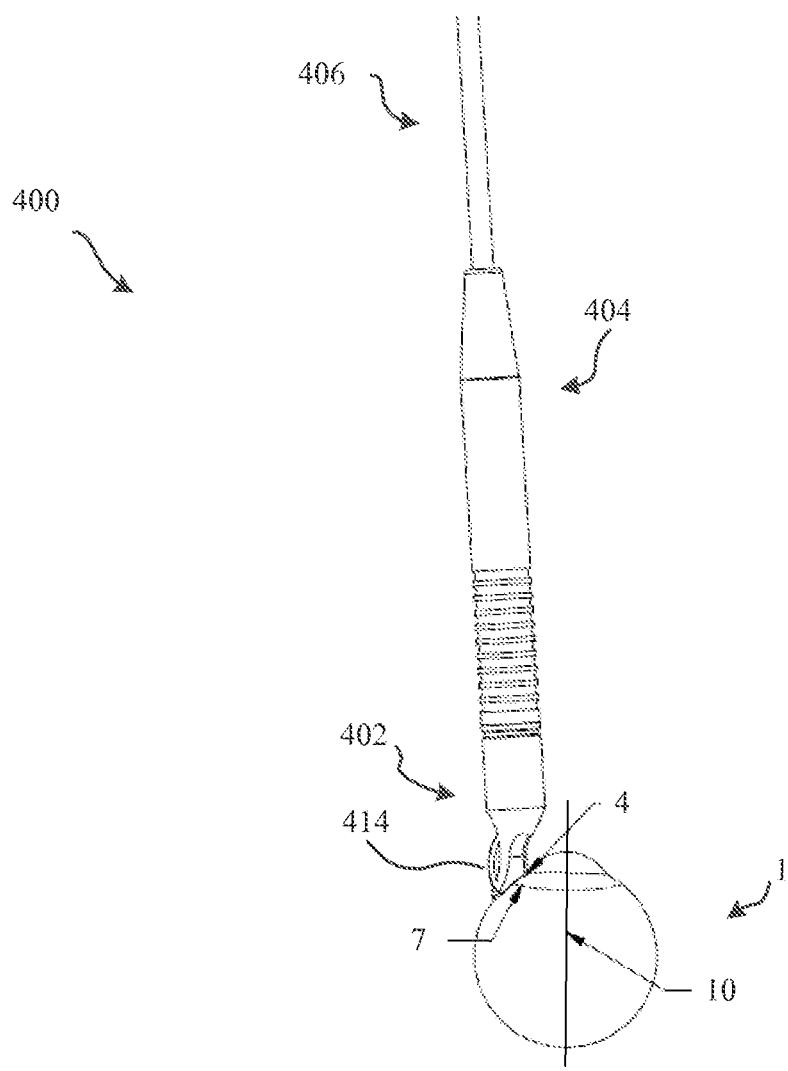

FIGS. 6A-6C illustrate yet another exemplary treatment probe 400. FIG. 6A shows a distal portion of treatment probe 400. FIG. 6B shows a close up view of an output tip 402 of treatment probe 400. FIG. 6C shows an exemplary placement of treatment probe 400 against a surface of the eye 1. Treatment probe 400 may include an output tip 402 coupled with a distal end of a handle 404, and a cord 406 configured to couple handle 404 with a console (e.g., console 12 of FIG. 2). Treatment probe 400 may further include an output tip 402 with a contact surface 408 geometry (e.g., side relief 416, side edges 417, placement edge 418, etc.) similar to output tip 102 that allows output tip 402 to rest against the sclera 2 and contour to the limbus 4 of the eye 1, as described above. Treatment probe 400 may further include a treatment fiber 412 and opening 410a similar to treatment probe 100. The distal ends of light pipe(s) 414 may terminate at the contact surface 408 at openings 410b. Openings 410b may be positioned distally from a distal end of treatment fiber 412 at opening 410a. The distal ends of the light pipes 414 may be adhered to the output tip 402 using adhesive and may be polished flush with contact surface 408. In order to position distal ends of light pipe(s) 414 at a distal portion of contact surface 408, light pipes 414 may pass through openings 410c before passing back through output tip 402 at openings 410b. Thus, the light pipe(s) 414 may be exposed for about 0.5 inches between opening 410c and 410b. With the distal ends of light pipe(s) 414 positioned distally from the distal end of treatment fiber 412, treatment probe 400 may apply illumination light directly behind the treatment site in order to illuminate the edge of the ciliary process 7 below the sclera 2 of the eye 1.

Figure 7A:
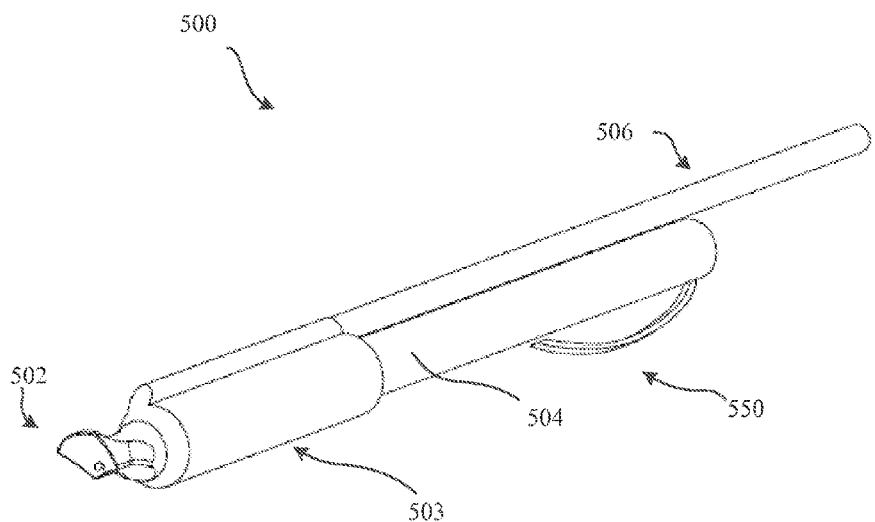
FIGS. 7A-7C show yet another exemplary treatment probe according to some embodiments of the invention.
Figure 7B:
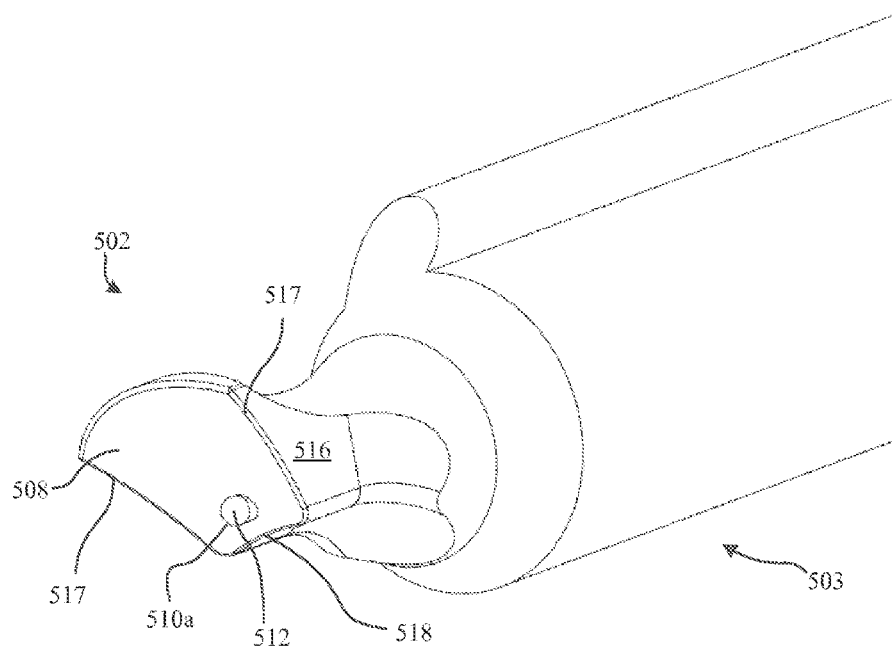
Figure 7C:
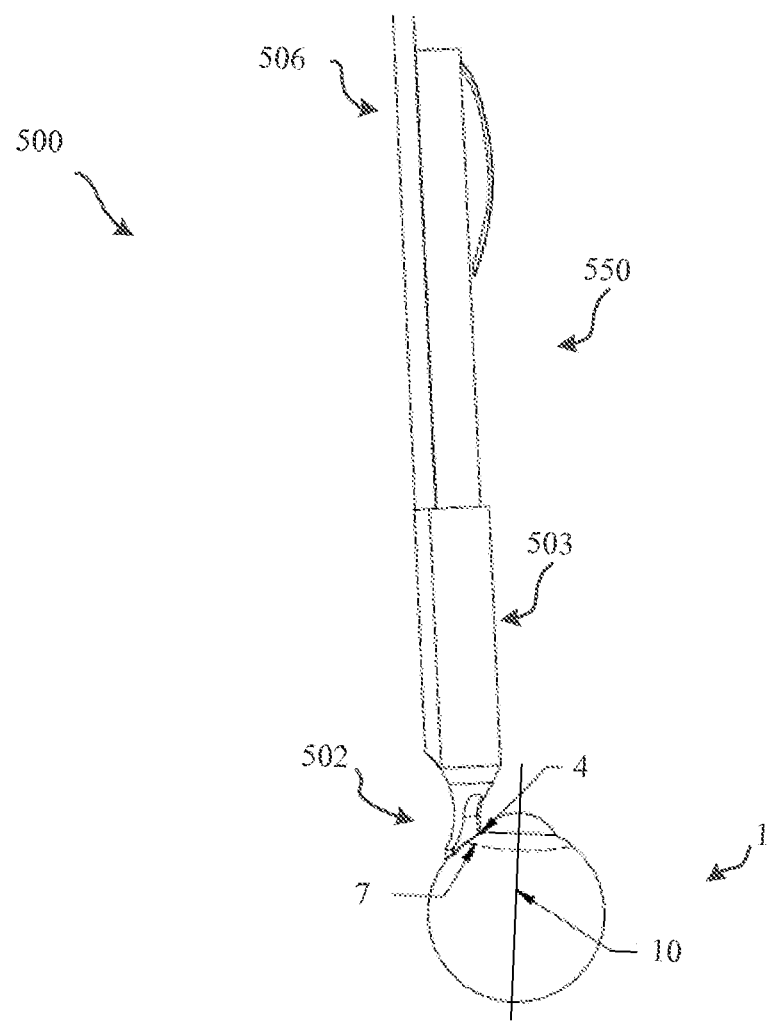

FIGS. 7A-7C illustrate yet another exemplary treatment probe 500. FIG. 6A shows a distal portion of treatment probe 500. FIG. 7B shows a close up view of an output tip 502 of treatment probe 500. FIG. 7C shows an exemplary placement of treatment probe 500 against a surface of the eye 1. Treatment probe 500 may include an output tip 502 coupled with a distal end of a receptacle 503, and a cord 506 configured to couple receptacle 503 with a console (e.g., console 12 of FIG. 2). Treatment probe 500 may further include an output tip 502 with a contact surface 508 geometry (e.g., side relief 516, side edges 517, placement edge 518, etc.) similar to output tip 102 that allows output tip 502 to rest against the sclera 2 and contour to the limbus 4 of the eye 1, as described above. Treatment probe 500 may further include a treatment fiber 512 and opening 510*a* similar to treatment probe 100. Output tip 502 may include a receptacle 503 at a proximal end of output tip 502. Receptacle 503 may be configured to receive and couple with a common physician pen light 550. Pen light 550 may, for example, be inserted into the output tip 502 receptacle 503 and may act as a handle 504 for treatment probe 500. The treatment fiber 512 may run along the receptacle 503 toward opening 510*a*. Optionally, a portion of output tip 502 may comprise a transparent material such as polycarbonate so as to allow illumination of the edge of the ciliary process 7 by the pen light 550.

It is to be understood that the above description is intended to be illustrative and not restrictive. For example, in some embodiments, the fiber optic 112, 212, 312, 412, 512 could be equipped with a beamshaping surface, contour, device or crystal tip, and such might also extend past the contact surface instead of the fiber optic itself.

Figure 8:
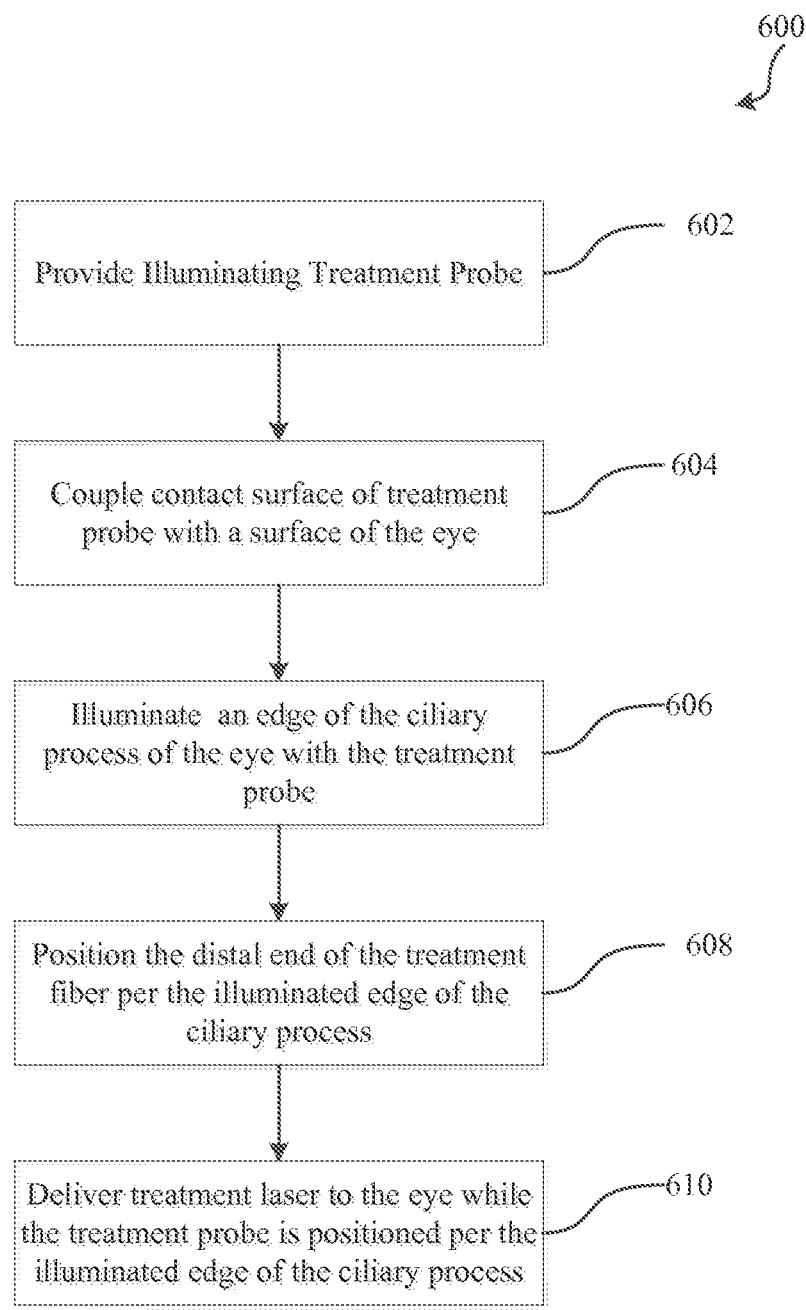
FIG. 8 shows an exemplary method according to some embodiments of the invention.

FIG. 8 shows and exemplary method 600 for treating an eye of a patient. At step 602, a treatment probe (e.g., treatment probe 100, 200, 300, 400, 500, etc.) for treating the eye of the patient may be provided. The treatment probe may include a treatment fiber for delivering a treatment laser energy to the eye from a distal end of the treatment fiber and an illumination fiber for delivering illuminating light to the eye from a distal end of the illumination light pipe. The treatment probe may further include a contact surface for coupling with a surface of the eye. At step 604, the contact surface of the treatment probe may be placed on the surface of the eye of the patient. At step 606, an edge of the ciliary process of the eye may be illuminated by directing illuminating light from the distal end of the illumination light pipe of the treatment probe to the eye. At step 608 the distal end of the treatment fiber of the treatment probe may be positioned per the illuminated edge of the ciliary process. At step 610, the treatment laser energy may be delivered to the eye from the distal end of the treatment fiber while the treatment probe is positioned per the illuminated edge of the ciliary process.

As described above, some treatment probes may be configured to illuminate the edge of the ciliary process of the eye by delivering illumination light at an angle ranging from 30-60° from the visual axis of the eye. Some treatment probes may illuminate the edge of the ciliary process by delivering illumination light through the cornea and parallel to the visual axis of the eye of the patient. Optionally, the illumination light may be delivered through the pupil of the eye of the patient. In other embodiments, the ciliary process may be illuminated by delivering illumination light through the cornea directly at the angle of the anterior chamber.

In some embodiments a distal end of the illumination light pipe may be manually adjustable such that the illumination light pipe is reconfigurable to deliver light at different angles relative to the eye and/or to different regions of the eye. Thus, some methods may include a step of adjusting the distal end of the illumination light pipe such that illumination light is delivered at a preferred angle or at a preferred structure of the eye.

In yet another embodiment, a treatment probe for treating an eye of a patient for glaucoma may be provided where the treatment probe houses a light source with a light transmitting surface oriented for delivering a treatment beam to the eye from the distal end of the elongate body. The treatment probe may also house an illumination light source that is configured for delivering illuminating light to the eye from a distal end of the body. For example, a treatment probe may house one or more laser diodes, one or more light emitting diodes, or combinations thereof for providing illumination light and treatment light to an eye. Advantageously, such embodiments may be configured to operate independently from a laser console. Some embodiments may couple with a separate power source, or may house a battery for powering the one or more laser diodes and/or the one or more light emitting diodes.

Figure 9:
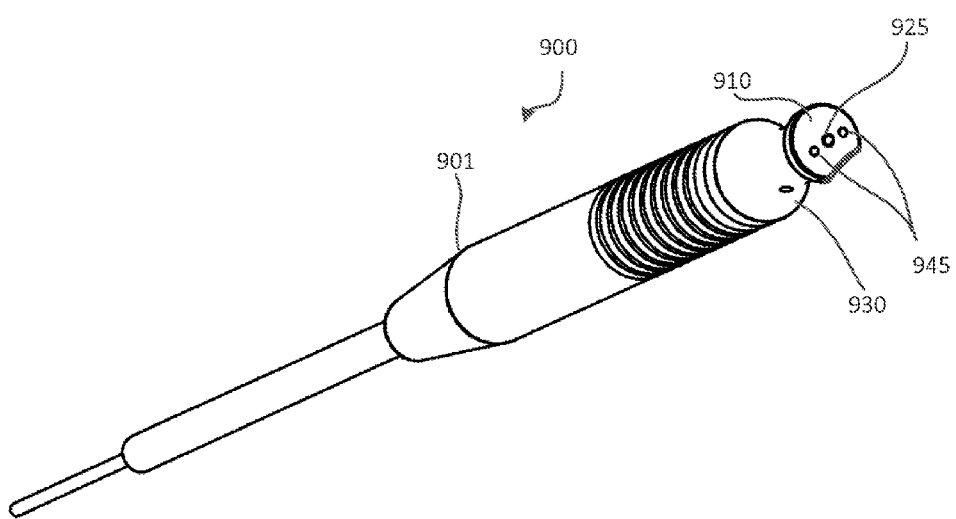
FIG. 9 shows an exemplary device with a convex contact surface.

FIG. 9 illustrates another exemplary device according to some embodiments of the invention. Exemplary handpiece 900 may include an elongate body 901 and an end portion/contact member 930 disposed on the distal end of elongate body 901. End portion/contact member 930 comprises a convex contact or other contact surface 910 that does not conform to the shape of the sclera. The elongate body 901 may house a treatment fiber and a distal end 925 of the treatment fiber may terminate at the convex contact surface 910. In some embodiments, the distal end 925 of the treatment fiber terminates at a position 2-4 mm from an edge of the contact surface 910. The elongate body 901 may also house one or more illumination fibers for illuminating a target region of the eye. The distal end 935 of the one or more illumination fibers may terminate at the convex contact surface 910 at positions spaced apart from the distal end 925 of the treatment fiber.

While illustrated with illumination fibers that terminate at the contact surface 910, it should be understood that many of the configurations described above may be used with embodiments with a convex contact surface. Accordingly, in some embodiments, the illumination fibers may deliver illumination light at an angle (e.g., 30-60°) from the visual axis of the eye while the contact surface of the probe is placed on the surface of the eye. Some embodiments may have illumination fibers which deliver illuminating light through the cornea and parallel to the visual axis of the eye. Optionally, the distal end of the illumination light conduit may be adjustable such a practitioner may selective adjust the delivery of the illumination light to other parts of the eye (e.g., the pupil of the eye, etc.). In some embodiments, the distal end of the illumination light conduit may be adjusted such that illumination light is delivered directly at the angle of the anterior chamber while the contact surface of the probe is placed on the surface of the eye.

Advantageously, the convex configuration of the contact surface 910 may facilitate sliding of the probe along the surface of the eye. In some embodiments, the convex contact surface and the sliding motion may introduce variability in the position and/or the angle of treatment delivery. Surprisingly, the variability in the position and/or the angle of treatment delivery may be beneficial to some patients.

In some embodiments, treatment probe 900 may be positioned to deliver treatment laser energy to a target region of the eye using the illumination of the target region. In some embodiments, the probe may be positioned to deliver treatment laser energy generally perpendicular to the surface of the eye. The probe 900 may then be gradually slid along an arc about the treatment region while exposing the targeted region of the eye (e.g., the pars plana) to pulsed laser energy.

A treatment arc may be a 180° arc or less in some embodiments. For example, a probe may be slid along an arc of 100° to 160°. Optionally, the arc may start at the 10 o'clock or 300° position of the eye and be swept to the 2 o'clock or 60° position, all the while exposing the targeted region of the eye, e.g., the pars plana, to pulsed laser energy. In some embodiments, a superior treatment arc of 150° can be created and an inferior treatment arc of 150° may be created. An inferior treatment arc may be created by positioning tip 925 about 3 mm posterior the limbus at the 8 o'clock position or 240° position and gradually sliding handpiece 900 until the tip 925 reaches the 4 o'clock position or 120°, all the while exposing the targeted region of the eye, e.g., the pars plana, with pulsed laser energy. Optionally, treatment arcs may be formed by a number of short strokes or incremental sweeps. For example, shorter incremental sweeps (e.g., 30°, 45°, 40°, 45°, 50°, 55°, 60° or the like) may be used to form full treatment arcs of a desired length (e.g., 100°, 120°, 150°, 180°, or the like).

As discussed above, use of a convex contact surface and a sliding treatment delivery technique may beneficially add variability in the treatment position and angle as the treatment probe is slid along the surface of the eye in one or more traverses.

In exemplary embodiments, the duration of laser energy exposure for each treatment arc may be 30-60 seconds (e.g., 45-55 seconds, 50 second, or the like). In some embodiments, several traverses of along the arc may be completed during the duration of laser energy exposure. For example, in some embodiments 1-20 traverses along the arc may be completed during the duration of laser energy exposure. In some embodiments it may be preferable to complete approximately 5-10 traverses along an arc of approximately 150° during a 50 second duration of laser energy exposure. Based on estimates for average adult human eye anatomy of 12.3 mm globe radius and 6 mm limbal radius, then an arc of laser treated tissue positioned 3 mm posterior to the limbus and covering an angle of 150° (e.g., 5 clock-hours) may be approximately 22 mm in length. Sweeping over this arc 5 times, for example, represents a total length of 110 mm. If this representative length is treated in 50 seconds, say, then this represents a linear sweep speed of about 110/50=2.2 mm/s. A fiber optic tip of 0.6 mm diameter will therefore be directly irradiating tissue directly below it for only approximately 0.6/2.2=0.27 s. This "dwell time" is approximately an order of magnitude less than the multi-second (often 2-5 seconds) cyclophotocoagulation dwell times typically used for coagulative destruction of ciliary tissue. This short dwell time helps reduce or eliminate excessive tissue temperatures that can result in tissue necrosis or even disruptive "pops" due to boiling of subsurface ocular tissue. It also helps explain the milder tissue effects and postoperative symptoms typically associated with this treatment hardware and techniques vs. other cyclodestructive procedures. The sweeping technique also imposes a more uniform time-temperature profile on ocular tissue than is possible to achieve using a "pick, place, and dwell" technique common to other cyclodestructive procedures. Long exposures to static targets can results in on-axis tissues that are overtreated with excessive temperature excursions (sometimes to the point of necrosis), nearby tissues that receive a more optimal thermal profile, and more peripheral tissues that are less optimally treated.

The peak power of the laser may be 2 watts. A total of 31,250 pulses at a rate of 625 pulses per second may be made during an exposure of 50 seconds duration. Each pulse may have an energy of 1.0 mJ. This represents energy delivery at a rate of 625 mJ/s, or an average power of 0.625 W. This value contrasts significantly when compared with the laser power setting of 1.5 to 2.5 W typically used with other cyclodestructive techniques. Like the sweeping technique described earlier, this lower average power setting may also help reduce the peak temperatures imposed on target tissues during laser treatment and avoids unnecessary tissue destruction.

Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications may be made without departing from the scope of the claims below.

What is claimed is:

1. A method for treating an eye of a patient, the eye having a sclera, a cornea, a pupil, a visual axis, and a ciliary process, and being afflicted with glaucoma, the method comprising:
   providing a treatment probe for treating the eye of the patient, the treatment probe including a treatment fiber for delivering a treatment laser energy to the eye from a distal end of the treatment fiber, an illumination light conduit for delivering illuminating light to the eye from a distal end of the illumination light conduit, and a contact surface for coupling with a surface of the eye;
   placing the contact surface of the treatment probe on the sclera of the eye of the patient;
   illuminating an edge of the ciliary process of the eye by directing illuminating light from the distal end of the illumination light conduit of the treatment probe through a surface of the eye to the ciliary process;
   positioning the distal end of the treatment fiber of the treatment probe against a surface of the sclera based on the illuminated edge of the ciliary process;
   delivering the treatment laser energy to the eye from the distal end of the treatment fiber and through the sclera while the treatment probe is positioned based on the illuminated edge of the ciliary process.

2. The method of claim 1, wherein illuminating the edge of the ciliary process of the eye with illuminating light from the illumination light conduit of the treatment probe comprises delivering illumination light at an angle ranging from 30-60° from the visual axis of the eye.

3. The method of claim 1, wherein illuminating the edge of the ciliary process of the eye with illuminating light from the illumination light conduit of the treatment probe comprises delivering illumination light through the cornea and parallel to the visual axis of the eye of the patient.

4. The method of claim 3, wherein the illumination light is delivered through the pupil of the eye of the patient.

5. The method of claim 1, wherein illuminating the edge of the ciliary process of the eye with illuminating light from the illumination light conduit of the treatment probe comprises delivering illumination light through the cornea directly at the angle of the anterior chamber.

6. The method of claim 1, wherein the distal end of the illumination light conduit is manually adjustable such that the illumination light conduit is reconfigurable to deliver light at different angles relative to the eye and/or to different regions of the eye.

7. The method of claim 6, further comprising adjusting the distal end of the illumination light conduit such that illumination light is delivered through the cornea and parallel to the visual axis of the eye while the contact surface of the probe is placed on the surface of the eye.

8. The method of claim 7, wherein adjusting the distal end of the illumination light conduit comprises adjusting the distal end of the illumination light conduit such that illumination light is delivered through the pupil of the eye.

9. The method of claim 6, further comprising adjusting the distal end of the illumination light conduit such that illumination light is delivered at an angle ranging from 30-60° from the visual axis of the eye while the contact surface of the probe is placed on the surface of the eye.

10. The method of claim 1, wherein the treatment probe houses the treatment light source and the illumination light source.

11. The method of claim 10, wherein the treatment light source comprises a laser diode.

12. The method of claim 10, wherein the treatment light source comprises a light emitting diode.

13. A method for treating an eye of a patient, the eye having a cornea, a pupil, a visual axis, and a ciliary process, and being afflicted with glaucoma, the method comprising:
providing a treatment probe for treating the eye of the patient, the treatment probe including a treatment fiber for delivering a treatment laser energy to the eye from a distal end of the treatment fiber, an illumination light conduit for delivering illuminating light to the eye from a distal end of the illumination light conduit, and a contact surface for coupling with a surface of the eye, wherein the distal end of the illumination light conduit is manually adjustable such that the illumination light conduit is reconfigurable to deliver light at different angles relative to the eye and/or to different regions of the eye;
placing the contact surf ace of the treatment probe on the surface of the eye of the patient;
illuminating an edge of the ciliary process of the eye by directing illuminating light from the distal end of the illumination light conduit of the treatment probe to the eye;
adjusting the distal end of the illumination light conduit such that illumination light is delivered at an angle ranging from 30-60° from the visual axis of the eye while the contact surface of the probe is placed on the surface of the eye;
adjusting the distal end of the illumination light conduit such that illumination light is delivered directly at the angle of the anterior chamber while the contact surface of the probe is placed on the surface of the eye;
positioning the distal end of the treatment fiber of the treatment probe based on the illuminated edge of the ciliary process;
delivering the treatment laser energy to the eye from the distal end of the treatment fiber while the treatment probe is positioned based on the illuminated edge of the ciliary process.

* * * * *

UNITED STATES PATENT AND TRADEMARK OFFICE
CERTIFICATE OF CORRECTION

PATENT NO. : 9,629,749 B2
APPLICATION NO. : 14/630561
DATED : April 25, 2017
INVENTOR(S) : Vold et al.

It is certified that error appears in the above-identified patent and that said Letters Patent is hereby corrected as shown below:

Column 16, Claim 13, Line 10, replace "sur face" with --surface--.

Signed and Sealed this
Tenth Day of July, 2018

Andrei Iancu
*Director of the United States Patent and Trademark Office*